United States Patent
Earl et al.

(10) Patent No.: US 9,211,189 B2
(45) Date of Patent: Dec. 15, 2015

(54) TRANSIENTLY MOBILE TIBIAL ENGAGEMENT

(75) Inventors: Brian D. Earl, South Bend, IN (US); Adam H. Sanford, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 908 days.

(21) Appl. No.: 12/618,050

(22) Filed: Nov. 13, 2009

(65) Prior Publication Data

US 2010/0125339 A1   May 20, 2010

Related U.S. Application Data

(60) Provisional application No. 61/114,698, filed on Nov. 14, 2008.

(51) Int. Cl.
   *A61F 2/38* (2006.01)
   *A61F 2/30* (2006.01)

(52) U.S. Cl.
   CPC .............. *A61F 2/3868* (2013.01); *A61F 2/389* (2013.01); *A61F 2002/30387* (2013.01); *A61F 2220/0025* (2013.01)

(58) Field of Classification Search
   CPC ................. A61F 2/3868; A61F 2/389; A61F 2002/30387; A61F 2220/0025
   USPC ..................... 623/20.32, 20.33, 20.15, 20.21, 623/20.14–20.34, 20.29
   See application file for complete search history.

(56) References Cited

U.S. PATENT DOCUMENTS

| | | | |
|---|---|---|---|
| 4,216,549 A * | 8/1980 | Hillberry et al. ........... | 623/20.26 |
| 4,257,129 A * | 3/1981 | Volz ............................ | 623/20.33 |
| 5,358,531 A * | 10/1994 | Goodfellow et al. ...... | 623/20.29 |
| 5,413,604 A | 5/1995 | Hodge | |
| 5,871,545 A | 2/1999 | Goodfellow et al. | |
| 5,964,808 A * | 10/1999 | Blaha et al. ................ | 623/20.28 |
| 6,080,195 A * | 6/2000 | Colleran et al. ........... | 623/20.32 |

(Continued)

FOREIGN PATENT DOCUMENTS

| | | |
|---|---|---|
| DE | 4102509 A1 | 7/1992 |
| DE | 4102509 C2 | 6/1996 |
| EP | 0904748 A2 | 3/1999 |
| EP | 0904748 A3 | 1/2000 |

(Continued)

OTHER PUBLICATIONS

The International Search Report and Written Opinion mailed in related International application No. PCT/US2009/064343 on Jan. 8, 2010.

*Primary Examiner* — Christopher D Prone
(74) *Attorney, Agent, or Firm* — Schwegman Lundberg & Woessner, P.A.

(57) ABSTRACT

The present invention relates to a tibial prosthesis having an articulating component and a tray component. The articulating component is configured for attachment to the tray component. Additionally, the articulating component may be attached to the tray component in a first condition in which the articulating component is at least rotatable relative to the tray component. This allows for the tray component to be attached to the tibia in a position that provides for proper rotation of the tray component with respect to the tibia and/or prevents the tray component from overhanging the resected tibia. Then, the articulating component may be rotated and/or translated to a position that provides for proper alignment of the articulating component with a femoral prosthesis. Once in this positioned, a locking mechanism is used to rotationally fix the articulating component to the tray component.

14 Claims, 4 Drawing Sheets

(56) References Cited

U.S. PATENT DOCUMENTS

| | | |
|---|---|---|
| 6,660,039 B1 | 12/2003 | Evans et al. |
| 6,770,098 B1 | 8/2004 | Hauri et al. |
| 7,740,662 B2 * | 6/2010 | Barnett et al. ............. 623/20.33 |
| 2003/0009232 A1 | 1/2003 | Metzger et al. |
| 2004/0034432 A1 * | 2/2004 | Hughes et al. ............. 623/20.28 |
| 2004/0215345 A1 | 10/2004 | Perrone, Jr. et al. |
| 2006/0015185 A1 | 1/2006 | Chambat et al. |

FOREIGN PATENT DOCUMENTS

| | | |
|---|---|---|
| EP | 0904748 B1 | 12/2005 |
| FR | 2794640 A1 | 12/2000 |
| FR | 2824260 A1 | 11/2002 |
| FR | 2833479 A1 | 6/2003 |
| FR | 2846875 A1 | 5/2004 |
| FR | 2893497 A1 | 5/2007 |
| WO | WO2004/069105 A1 | 8/2004 |

* cited by examiner

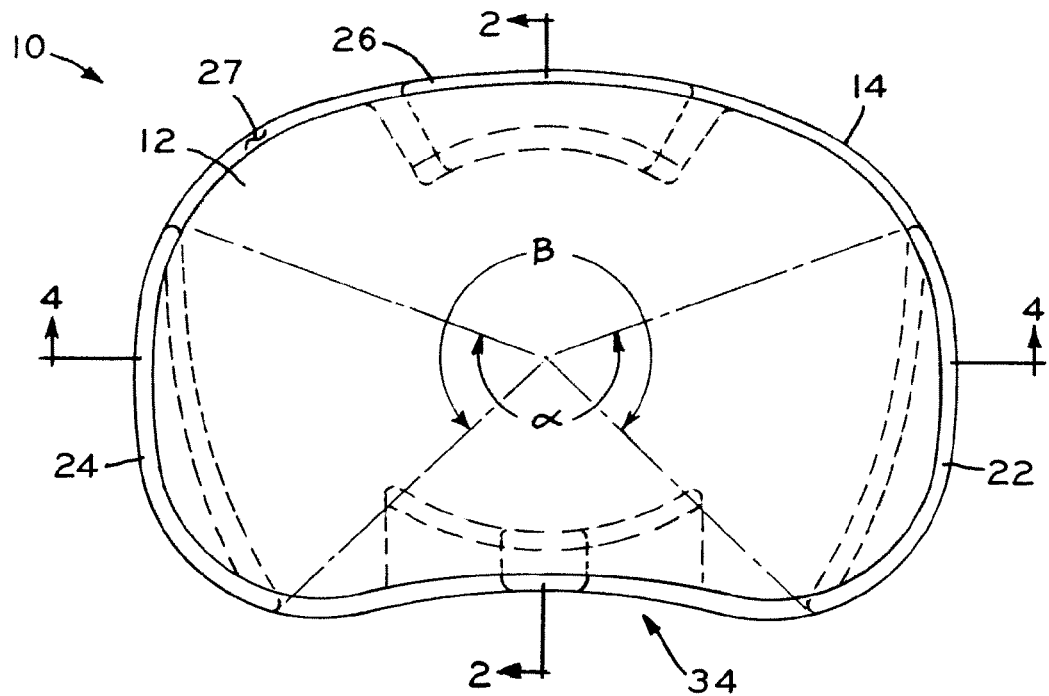
FIG_1
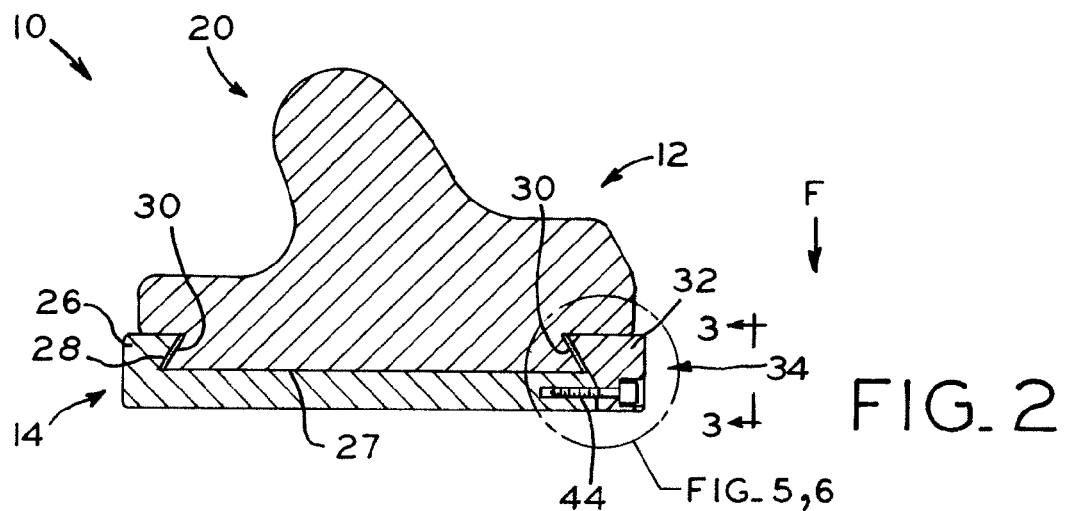
FIG_2
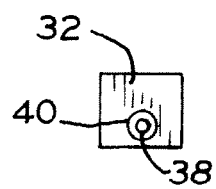
FIG_3

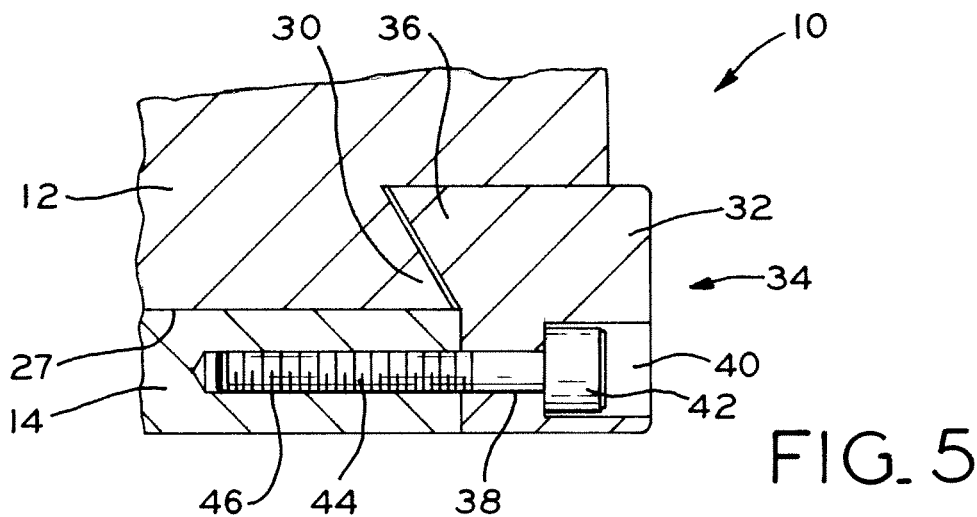
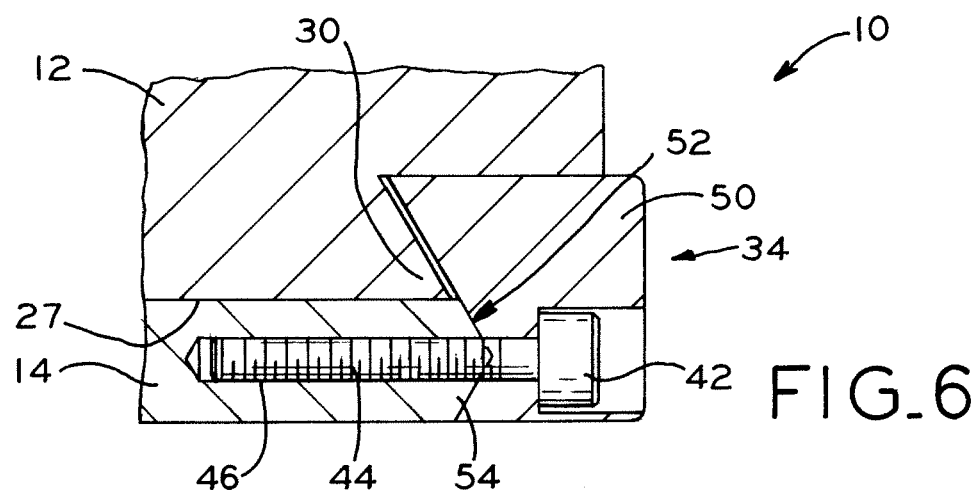

TRANSIENTLY MOBILE TIBIAL ENGAGEMENT

CROSS-REFERENCE TO RELATED APPLICATIONS

This application claims the benefit under Title 35 U.S.C. §119(e) of U.S. Provisional Patent Application Ser. No. 61/114,698, entitled TRANSIENTLY MOBILE TIBIAL ENGAGEMENT, filed on Nov. 14, 2008, the disclosure of which is expressly incorporated by reference herein.

BACKGROUND

1. Field of the Invention

The present invention relates to orthopedic prostheses and, particularly, to tibial prostheses.

2. Description of the Related Art

Orthopedic prostheses are commonly utilized to repair and/or replace damaged bone and tissue in the human body. For example, a knee prosthesis may be implanted during a total knee arthroplasty to replace damaged or destroyed bone in the tibia and/or femur and to recreate the natural, anatomical articulation of the knee joint. A femoral prosthesis may be shaped to replicate one or both of the natural femoral condyles. After resecting the distal end of the femur, one side of the femoral prosthesis is secured to the bone stock of the femur and the opposing side of the femoral prosthesis is configured for articulation against a tibial prosthesis.

A tibial prosthesis may include a first, articulating component having a concave condylar portion configured for articulation against the femoral prosthesis. The articulating component of the tibial prosthesis may be secured to a tray component that has an opposing side for securing the tibial prosthesis to the bone stock of a resected proximal tibia. By securing the articulating component of the tibial prosthesis to the tray component to prevent translation and rotation of the articulating component relative to the tray component, a fixed bearing tibial component is created. The articulating component of the tibial prosthesis may be made from a polymer to facilitate articulation with the femoral component, while the tray component of the tibial prosthesis may be made from a metal to provide additional strength and rigidity to the tibial prosthesis.

When implanting a fixed bearing tibial prosthesis during a total knee arthroplasty, a surgeon attempts to balance the effects of several competing factors. First, the surgeon may attempt to ensure that the tibial prosthesis is implanted in its most desirable rotational position with respect to the resected proximal tibia. In setting the most desirable rotational position of the tibial prosthesis with respect to the resected proximal tibia, the surgeon may attempt to maximize tibial bone coverage and/or position the tibial prosthesis in a rotational position that also does not overhang, i.e., extend outward beyond, the resected proximal tibia. Undercoverage of the resected proximal tibia is associated with concerns of subsidence of the tibial prosthesis over time, whereas overhang is associated with concerns of soft tissue impingement. By implanting the tibial prosthesis in the most desirable rotational position with respect to the resected proximal tibia, the likelihood of subsidence, instability in the tibia, and soft tissue impingement are reduced.

Alternatively, the surgeon may attempt to position the tibial prosthesis on the resected proximal tibia at a position in which it is most desirably rotated with respect to the femoral prosthesis. Thus, the surgeon would implant the tibial prosthesis at a position that provides the best conformity between the femoral prosthesis and the tibial prosthesis during knee articulation. By implanting the tibial prosthesis in the most desirable rotational position with respect to the femoral prosthesis, potential difficulties in balancing the knee joint and in creating proper varus/valgus alignment may be avoided. However, implanting the tibial prosthesis at a position in which it is in the most desirable rotational position with respect to the femoral prosthesis may not result in the implantation of the tibial prosthesis in the most desirable rotational position with respect to the resected proximal tibia.

In order to address these concerns, mobile tibial bearing prostheses have been developed. However, for certain patients, the use of a mobile tibial bearing prosthesis may be contraindicated.

SUMMARY

The present invention provides a tibial prosthesis having an articulating component and a tray component. The articulating component is configured for attachment to the tray component. Additionally, the articulating component may be attached to the tray component in a first condition in which the articulating component is at least rotatable relative to the tray component. This allows for the tray component to be attached to the tibia in a position that provides for proper rotation and/or alignment of the tray component with respect to the tibia to achieve maximum tibial bone coverage and/or to prevent or minimize the tray component from overhanging the resected tibia. Then, the articulating component may be rotated and/or translated to a position that provides for proper, anatomical alignment of the articulating component with a femoral prosthesis. Once in the desired position, a locking mechanism is used to rotationally and/or translationally fix the articulating component to the tray component. This allows the articulating component to be placed in a second condition in which the articulating component is rotationally and translationally fixed to the tray component to form a fixed bearing tibial prosthesis.

In order to implant the tibial prosthesis of the present invention, the tray component is implanted and secured to the resected proximal tibia of a patient in a position that maximizes coverage of the resected proximal tibia by the tray component and/or minimizes plate overhang of the resected proximal tibia. Then, the articulating component may be secured to the tray component in the first condition in which it is at least rotatable relative to the tray component. The surgeon may then trial the tibial prosthesis while the articulating component of the tibial prosthesis is allowed to rotate and/or translate into a position that provides for the most desirable articulation with the femur and/or femoral prosthesis, i.e., the articulating component self-aligns to optimize its position during joint articulation. Specifically, due to the ability of the articulating component of the tibial prosthesis to rotate and/or translation relative to the tray component, the articulating component will rotate and/or translate into a position in which it is properly aligned with the femoral prosthesis as the knee of the patient is flexed or otherwise manipulated during a trial reduction. Alternatively, the surgeon may manually set the articulating component in the desired rotational and/or translational orientation relative to the tray component. Once in this position, a locking mechanism is secured to the articulating component and/or tray component to place the articulating component in a second condition in which it is rotationally and/or translationally fixed to the tibial tray.

In one form thereof, the present invention provides a tibial prosthesis including a tray component having a superior surface; an articulating component moveably secured to the tray component, the articulating component at least one of translatable and rotatable relative to the tray component in a plane parallel to the superior surface of the tray component, the articulating component lockable in a plurality of differing positions, the plurality of differing positions differing from one another by at least one of translation and rotation; and a lock securable to at least one of the tray component and the articulating component to fix the rotational and translational position of the articulating component relative to the tray component in a number of different ones of the plurality of differing positions.

In another form thereof, the present invention provides a tibial prosthesis, including a tray component having a superior surface; an articulating component moveably secured to the tray component, the articulating component at least one of translatable and rotatable relative to the tray component in a plane parallel to the superior surface of the tray component, the articulating component lockable in a plurality of differing positions, the plurality of differing positions differing from one another by at least one of translation and rotation; and locking means for locking the rotational and translational position of the articulating component relative to the tray component in a number of different ones of the plurality of differing positions.

In yet another form thereof, the present invention provides a method of implanting a tibial prosthesis, including the step of positioning a tray component on a proximal tibia, with the tray component having a superior surface. The method also includes the step of moveably securing an articulating component to the tray component to form a tibial prosthesis, with the articulating component being at least one of translatable and rotatable relative to said tray component in a plane parallel to the superior surface of the tray component. The method also includes the step of locking the articulating component in one of a plurality of differing positions relative to the tray component, with the plurality of differing positions differing from one another by at least one of translation and rotation.

BRIEF DESCRIPTION OF THE DRAWINGS

The above-mentioned and other features and advantages of this invention, and the manner of attaining them, will become more apparent and the invention itself will be better understood by reference to the following descriptions of embodiments of the invention taken in conjunction with the accompanying drawings, wherein:

FIG. 1 is a plan view of an exemplary embodiment of a tibial prosthesis made in accordance with the present invention;

FIG. 2 is a cross-sectional view of the tibial prosthesis of FIG. 1 taken along line 2-2 of FIG. 1;

FIG. 3 is an elevational view of an exemplary embodiment of a locking mechanism of the tibial prosthesis of FIG. 1 taken in the direction of line 3-3 of FIG. 2;

FIG. 5 is an enlarged, fragmentary cross-sectional view of the tibial prosthesis of FIG. 1 depicting the portion of the tibial prosthesis encircled by dashed lines in FIG. 2;

FIG. 6 is an enlarged, fragmentary cross-sectional view of another exemplary embodiment of the tibial prosthesis of FIG. 1 depicting the portion of the tibial prosthesis that corresponds to the portion of the tibial prosthesis of FIG. 1 encircled by dashed lines in FIG. 2;

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 4:
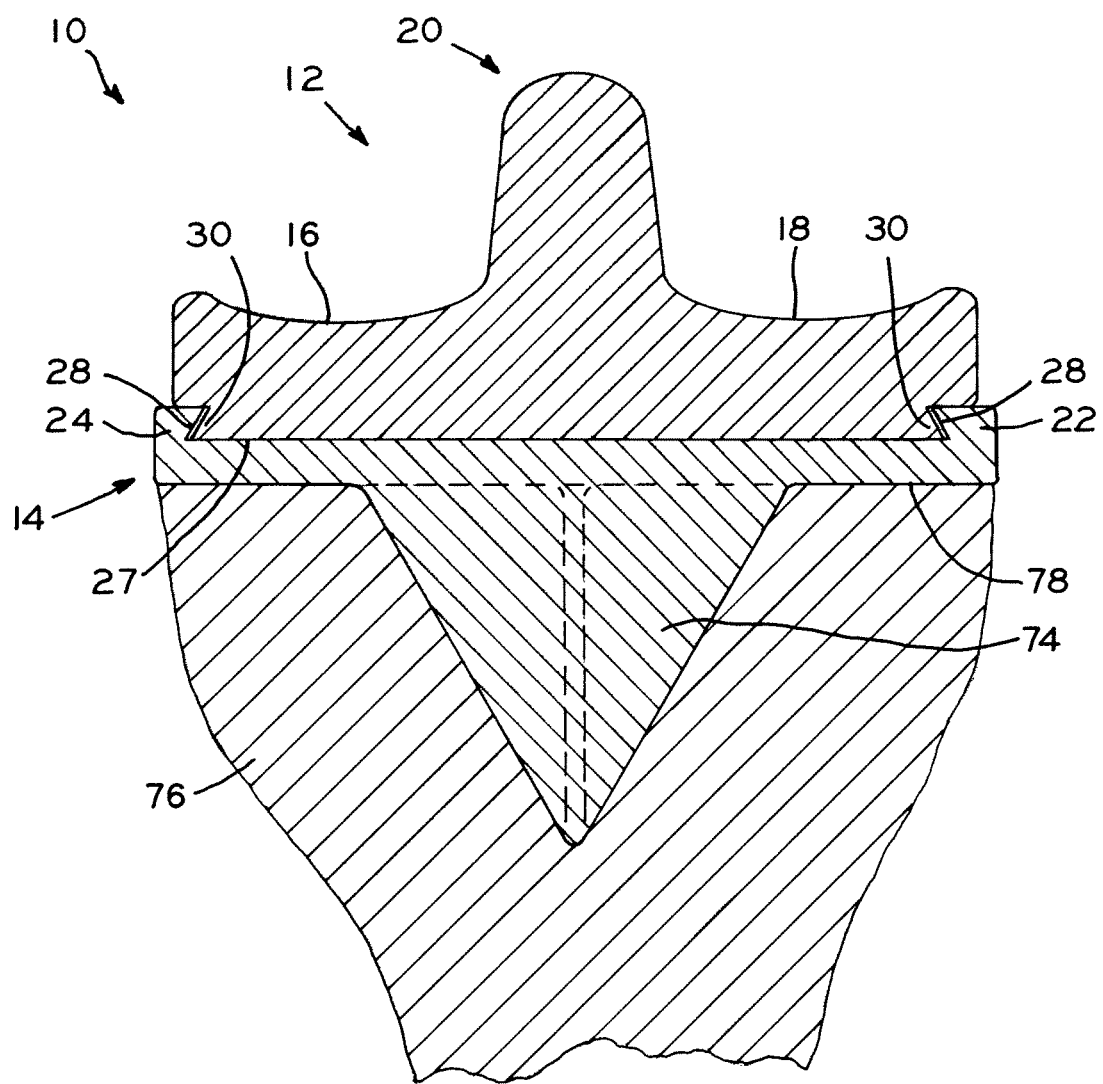
FIG. 4 is a cross-sectional view of the tibial prosthesis of FIG. 1 taken along line 4-4 of FIG. 1 and further depicting the tibial prosthesis implanted within a tibia.

Referring to FIGS. 1, 2, and 4, tibial prosthesis 10 is shown in an assembled condition and includes articulating component 12 and tray component 14. While shown and described herein with specific reference to a right knee application, tibial prosthesis 10 may also be configured for use in a left knee application. Referring to FIG. 4, articulating component 12 includes a pair of opposing, concave articulating surfaces 16, 18 that are configured for articulation against opposing convex condyles of a femur or femoral prosthesis (not shown). Tibial eminence 20 extends upwardly between opposing articulating surfaces 16, 18. While shown and described herein as including tibial eminence 20, it is envisioned that tibial eminence 20 may also be absent.

Referring to FIGS. 2 and 4, rails 22, 24, 26 project upwardly from superior surface 27 of tray component 14 and define interior dovetail-shaped grooves 28 that interact with corresponding dovetail projections 30 on articulating component 12. In this manner, the interaction of rails 22, 24, 26 of tray component 14 with projections 30 of articulating component 12 provide medial, lateral, and anterior stability, respectively, to tibial prosthesis 10, while also functioning to resist lift-off of articulating component 12.

In one exemplary embodiment, rails 22, 24 capture a portion of the periphery of articulating component 12, such as projections 30, to create a snap-fit connection of articulating component 12 to tray component 14 in a first condition. Due to the snap-fit connection between articulating component 12 and tray component 14, a snapping or popping sound may be heard when articulating component 12 is properly seated to tray component 14 and a stable connection between articulating component 12 and tray component 14 is formed. As a result of this configuration, a stable connection between articulating component 12 and tray component 14 is provided for trialing of tibial prosthesis 10, such as during range of motion testing, prior to rotationally and/or translationally locking articulating component 12 to tray component 14, as described in detail below.

To secure articulating component 12 to tray component 14, articulating component 12 is front loaded onto tray component 14, i.e., articulating component 12 is advanced in a posterior direction from a location anterior of tray component 14 until articulating component 12 has engaged tray component 14. For example, in one exemplary embodiment, articulating component 12 is snap-fit or otherwise secured to tray component 14 by advancing articulating component 12 in a posterior direction until the posterior portion of articulating component 12 contacts a posterior portion of tray component 14. In this position, the anterior portion of articulating component 12 may be positioned on and/or above anterior rail 26 of tray component 14. Then, a force may be applied to the anterior portion of articulating component 12 in the direction of superior surface 27 of tray component 14 that is sufficient to resiliently deform projections 30 of articulating component 12 and allow projections 30 to be received in grooves 38 of rails 22, 24, 26. In this manner, a snap-fit connection is formed between articulating component 12 and tray component 14 that secures articulating component 12 to tray component 14. In one exemplary embodiment, articulating component 12 is also captured by tray component 14 as a result of angle β extending more than 180 degrees in an anterior direction from the posterior-most portions of rails 22, 24. By extending from opposing posterior-most portions through at least 180 degrees, rails 22, 24 prevent articulating component 12 from translating off of tray component 14 in a posterior direction. In other exemplary embodiments, articulating component 12 may be secured to tray component 14 by advancing articulating component 12 along tray component 14 in other directions and/or orientations. For example, due to the resiliency of projections 30, articulating component 12 may, in exemplary embodiments, be back loaded onto tray component 14, i.e., articulating component 12 may be advanced in an anterior direction from a location posterior of tray component 14 until articulating component 12 has engaged tray component 14.

As indicated above, rails 22, 24, 26 and projections 30 are designed to allow articulating component 12 to at least rotate relative to tray component 14. In one exemplary embodiment, rails 22, 24, 26 are configured such that, with articulating component 12 positioned atop and centered on tray component 14, rails 22, 24, 26 are spaced a distance from projections 30, such that a gap is formed between rails 22, 24, 26 and projections 30. In one exemplary embodiment, rails 22, 24, 26 are spaced a few millimeters (mm) from corresponding projections 30, such that the gap formed between rails 22, 24, 26 and projections 30 may be as small as substantially 2 mm, 3 mm, 4 mm, or 5 mm, and as large as substantially 6 mm, 7 mm, 8 mm, 9 mm, or 10 mm, for example. In this embodiment, articulating component 12 is both rotatable and translatable relative to tray component 14. Additionally, in this embodiment, rails 22, 24, 26 and projections 30 are configured such that once articulating component 12 is snap-fit or otherwise secured to tray component 14 articulating component 12 cannot be translated in a direction away from and entirely off of tray component 14. Specifically, if articulating component 12 is translated in a direction away from tray component 14, at least two of rails 22, 24, 26 and projections 30 will engage one another before articulating component 14 can be translated into a position entirely off of tray component 14. The interaction of the at least two rails 22, 24, 26 and projections 30 will then prevent additional translation of articulating component 12 away from tray component 14, which prevents articulating component 12 from being translated entirely off of tray component 14.

When articulating component 12 is secured to and at least rotatable relative to tray component 14, articulating component 12 is attached to tray component 14 in a first condition. In one exemplary embodiment, articulating component 12 is rotatable relative to tray component 14 through a fixed range of motion. For example, articulating component 12 may be rotatable through a range of motion of between one and six degrees relative to tray component 14. However, other embodiments are contemplated in which articulating component 12 is rotatable through both greater and lesser ranges of motion, i.e., is rotatable by greater than or less than six degrees. For example, in exemplary embodiments, angle α may be as small as 1 degree, 2 degrees, 3 degrees, 4 degrees, or 5 degrees and as large as 6 degrees, 7 degrees, 8 degrees, 9 degrees, or 10 degrees.

In one exemplary embodiment, angle α, shown in FIG. 1 and measured in a posterior direction between the anterior-most portions of medial and lateral rails 22, 24, extends around tray component 14 by more than 180°. In another exemplary embodiment, angle α extends around tray component by 195°. By designing rails 22, 24 so that an angle measured between the anterior-most portions of rails 22, 24 extends around tray component 14 through greater than 180°, translation of articulating component 12 relative to tray component 14 is limited and articulating component 12 is captured on tray component 14. Thus, in the embodiment shown in FIG. 1, once a portion of the periphery of articulating component 12 is captured by rails 22, 24, translation of articulating component 12 along tray component 14 in any direction is limited.

For example, in one exemplary embodiment, while it may be necessary to allow for slight translation of articulating component 12 relative to tray component 14 in order to provide for the rotation of articulating component 12 relative to tray component 14 described in detail above, translation of articulating component 12 relative to tray component 14 is substantially prevented once at least a portion of the periphery of articulating component 12 is captured by rails 22, 24. Thus, articulating component 12 may be prevented from translating along superior surface 27 of tray component 14 into a position in which any portion of articulating component 12 is not substantially supported by tray component 14, i.e., into a position in which articulating component 12 extends substantially beyond the perimeter of tray component 14.

However, in other embodiments, such as the embodiment discussed in detail above in which a gap is formed between rails 22, 24, 26 and projections 30, articulating component 12 is also translatable relative to tray component 14. In these embodiments, substantial translation of articulating component 12 relative to tray component 14 may be achieved. For example, articulating component 12 may translate along superior surface 27 of tray component 14 into a position in which articulating component 12 is not entirely supported by tray component 14, i.e., into a position in which articulating component 12 extends beyond the perimeter of tray component 14.

Additionally, while angle α, shown in FIG. 1 and measured in a posterior direction between the anterior-most portions of rails 22, 24, is described and depicted herein as extending around tray component 14 through greater than 180°, angle α may, in other exemplary embodiments, extend around tray component 14 through less than 180°. In these embodiments, locking mechanism 32 may be partially seated and/or secured within groove 34 such that translation of articulating component 12 in the direction of locking mechanism 32 is substantially prevented. As a result, articulating component 12 is prevented from translating along superior surface 27 of tray component 14 into a position in which any portion of articulating component 12 is substantially not supported by tray component 14, i.e., into a position in which articulating component 12 extends substantially beyond the perimeter of tray component 14. By partially seating and/or securing locking mechanism 32 within groove 34, a stable connection is provided between articulating component 12 and tray component 14 for trialing of tibial prosthesis 10, such as during range of motion testing, prior to rotationally locking articulating component 12 to tray component 14. Then, in order to rotationally lock articulating component 12 to tray component 14, locking mechanism 32 is fully seated and/or secured within groove 34 as described in detail above.

Referring to FIGS. 1-3 and 5, locking mechanism 32 is shown. As indicated above, locking mechanism 32 is configured for receipt within groove 34 defined by articulating component 12 and tray component 14. By fully seating and/or securing locking mechanism 32 within groove 34, articulating component 12 is placed in a second condition, i.e., a condition in which articulating component 12 is both translationally and rotationally fixed to tray component 14. In the exemplary embodiment, locking mechanism 32 generates a downward clamping force in the direction of arrow F (FIG. 2), which cooperates with rails 22, 24, 26 to translationally and rotationally fix articulating component 12 to tray component 14. Additionally, locking mechanism 32 may also include small radial interference ribs (not shown) that protrude into dovetail projections 30 of articulating component 12.

Locking mechanism 32 may be secured to articulating component 12 and/or tray component 14 in any manner. For example, locking mechanism 32 may form a snap-fit or an interference fit with articulating component 12 and/or tray component 14. Alternatively, locking mechanism 32 may be secured to articulating component 12 and/or tray component 14 using a fastener, such as a screw. Thus, depending on the method used for securing locking mechanism 32 to articulating component 12 and/or tray component 14, locking mechanism 32 may be formed from any biocompatible material, such as polyethylene or a biocompatible metal alloy.

Specifically, referring to FIG. 5, locking mechanism 32 is shown including dovetail projection 36 and bore 38. Bore 38 includes counterbore 40 in which head 42 of screw 44 is received. Screw 44 extends through bore 38 and threadingly engages bore 46 in tray component 14. Referring to FIG. 6, another exemplary embodiment of locking mechanism 32 is shown as locking mechanism 50. Locking mechanism 50 includes components that are identical or substantially identical to corresponding features of locking mechanism 32 and like reference numerals have been used to identify identical or substantially identical components therebetween. Locking mechanism 50 is secured to tray component 14 in a substantially similar manner and locking mechanism 32 and, once secured, functions to prevent rotation and/or translation of articulating component 12 relative to tray component 14. However, unlike locking mechanism 32, locking mechanism 50 includes a recess 52 that is designed to receive projection 54 that defines at least a portion of the periphery of tray component 14. By receiving projection 54 within recess 52, locking mechanism 50 provides an additional interaction with tray component 14 that functions to retain locking mechanism 50 in position and prevent rotation and/or translation of articulating component 12 relative to tray component 14.

Figure 7:
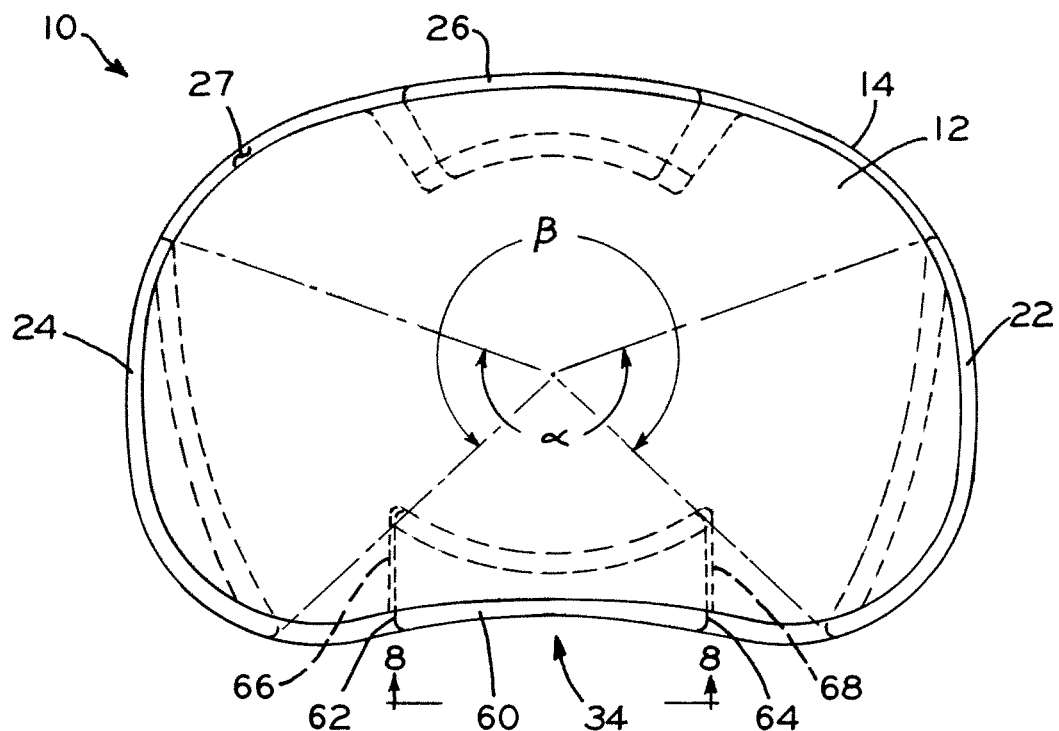
FIG. 7 is a plan view of an exemplary embodiment of a tibial prosthesis made in accordance with the present invention.
Figure 8:
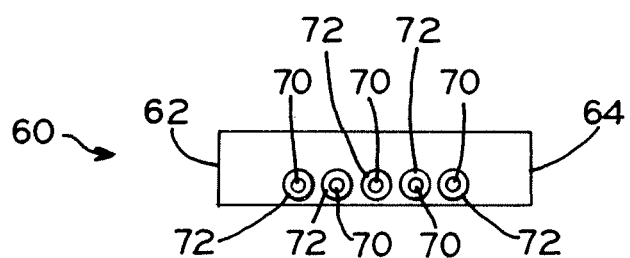
FIG. 8 is an elevational view of an exemplary embodiment of a locking mechanism of the tibial prosthesis of FIG. 7 taken in the direction of line 8-8 of FIG. 7.

Referring to FIGS. 7 and 8, another exemplary embodiment of locking mechanism 32 is shown as locking mechanism 60. Locking mechanism 60 includes components that are identical or substantially identical to corresponding features of locking mechanism 32 and like reference numerals have been used to identify identical or substantially identical components therebetween. Locking mechanism 60 is sized to substantially entirely fill groove 34. As a result, with locking mechanism 60 positioned within groove 34, opposing side walls 62, 64 of locking mechanism 60 interact with walls 66, 68 of articulating component 12 that partially define groove 34. In this manner, when secured to tibial tray 14, locking mechanism 60 provides an additional mechanism for preventing rotation and/or translation of articulating component 12 relative to tray component 14.

Referring to FIG. 8, locking mechanism 60 includes a plurality of bores 70 having corresponding counter bores 72 formed therein. When articulating component 12 is positioned as desired with respect to tray component 14, locking mechanism 60 is positioned with one of bores 72 aligned or substantially aligned with bore 46 (FIG. 5) in tray component 14. Then, screw 44 (FIG. 5) is advanced through the one of bores 70 that is aligned with or substantially aligned with bore 46 in tray component 14 and screw 44 is threadingly engaged with bore 46 in tray component 14 to secure locking mechanism 60 in position and to prevent rotation and/or translation of articulating component 12 relative to tray component 14.

Referring to FIG. 4, in order to implant tibial prosthesis 10, the proximal portion of a patent's tibia 76 is resected to provide a substantially flat surface 78 for the receipt of tray component 14. Once the proximal tibia is resected, tray component 14 is implanted, as shown in FIG. 4, and secured to the resected proximal tibia in a position that maximizes coverage of the resected proximal tibia by tray component 14 and/or positions tray component 14 with minimum overhang from the resected proximal tibia. In one exemplary embodiment, tray component 14 includes keel 74 that facilitates the retention of tray component 14 within the patient's tibia. Once tray component 14 is secured in position, articulating component 12 may be secured to tray component 14 in the first condition in which articulating component 12 is at least rotatable relative to tray component 14, i.e., before one of locking mechanisms 32, 50, 60 is fully seated and/or secured within groove 34. The surgeon may then trial tibial prosthesis 10 in conjunction with the patient's femur or a previously implanted femoral prosthesis (not shown) in a known manner. For example, the surgeon may perform range of motion testing. During the trialing, articulating component 12 may rotate and/or translate due to the interaction of tibial prosthesis 10 with the patient's femur and/or femoral prosthesis. The rotation and/or translation of articulating component 12 relative to tray component 14 during trialing results in the self-alignment of articulating component 12 with the patient's femur or femoral prosthesis.

Specifically, due to the ability of articulating component 12 of tibial prosthesis 10 to rotate and/or translate relative to tray component 14, as described in detail above, articulating component 12 may rotate and/or translate into a position in which it is properly aligned with the patient's femur and/or femoral prosthesis as the patient's knee joint is flexed or otherwise manipulated. For example, the surgeon may identify that articulating component 12 maintains a particular orientation relative to tray component 14 during a significant portion of the range of motion testing. This orientation of articulating component 12 relative to tray component 14 may then be fixed by fully seating and/or securing one of locking mechanisms 32, 50, 60 to articulating component 12 and/or tray component 14 to place articulating component 12 in the second condition in which articulating component 12 is rotationally and translationally fixed relative to tray component 14, as described in detail above. Alternatively, the surgeon may choose to manually align articulating component 12 in the desired rotational and/or translational orientation relative to tray component 14. Once in the desired position, one of locking mechanisms 32, 50, 60 is fully seated and/or secured to articulating component 12 and/or tray component 14 to place articulating component 12 in the second condition in which articulating component 12 is rotationally and translationally fixed relative to tray component 14, as described in detail above.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A tibial prosthesis, comprising:
a tray component having a superior surface;
an articulating component secured to said tray component, wherein in a first, movable condition, said articulating component being at least one of translatable and rotatable relative to said tray component in a plane parallel to said superior surface of said tray component, and in a second, fixed and locked condition, said articulating component being lockable in a plurality of differing positions relative to the tray component, said plurality of differing positions differing from one another by at least one of translation and rotation of the articulating component relative to the tray component; and
a lock securable to at least one of said tray component and said articulating component to fix and lock the rotational and translational position of said articulating component relative to said tray component in one of a selected rotational and translational position of said plurality of differing positions.

2. The tibial prosthesis of claim 1, wherein said articulating component is both translatable and rotatable relative to said tray component in a plane parallel to said superior surface of said tray component.

3. The tibial prosthesis of claim 1, wherein said articulating component is captured on said superior surface of said tray component and said articulating component is prevented from translating along said superior surface of said tray component into a position in which said articulating component is not entirely supported by said superior surface of said tray component.

4. The tibial prosthesis of claim 1, wherein said tray component and said articulating component cooperate to define a tibial prosthesis recess, said lock being at least partially received within said tibial prosthesis recess when said lock is secured to said at least of one of said tray component and said articulating component.

5. The tibial prosthesis of claim 4, wherein said articulating component further comprises a pair of opposing sidewalls cooperating to partially define said tibial prosthesis recess, wherein said lock is sized to extending substantially entirely between said opposing sidewalls of said articulating component.

6. The tibial prosthesis of claim 1, wherein said tray component further comprises a plurality of tray projections extending from said superior surface and said articulating component further comprises a plurality of articulating component recesses, said tray projections cooperating with said articulating component recesses to moveably secure said articulating component to said tray component.

7. The tibial prosthesis of claim 6, wherein said plurality of tray projections comprise dovetail projections and said plurality of articulating component recesses comprise dovetail recesses.

8. The tibial prosthesis of claim 6, wherein said plurality of tray projections includes a medial tray projection and a lateral tray projection, wherein an angle measured in an anterior direction from a posterior-most point of said medial tray projection to a posterior most point of said lateral tray projection and measured from an origin at a central point of the tray exceeds one-hundred and eighty degrees.

9. A tibial prosthesis, comprising:
a tray component having a superior surface;
an articulating component secured to said tray component, wherein in a first, movable condition, said articulating component being at least one of translatable and rotatable relative to said tray component in a plane parallel to said superior surface of said tray component, and in a second, fixed and locked condition, said articulating component being lockable in a plurality of differing positions relative to the tray component, said plurality of differing positions differing from one another by at least one of translation and rotation of the articulating component relative to the tray component; and
locking means for locking and fixing the rotational and translational position of said articulating component relative to said tray component in one of a selected rotational and translational position of said plurality of differing positions.

10. The tibial prosthesis of claim 9, wherein said locking means is secured to at least one of said tray component and said articulating component to lock the rotational and translational position of the articulating component relative to the tray component.

11. The tibial prosthesis of claim 10, wherein said locking means comprises a lock body that is at least partially received within a tibial prosthesis recesses defined by said tray component and said articulating component when said locking means is secured to said at least one of said tray component and said articulating component.

12. The tibial prosthesis of claim 11, wherein said articulating component further comprises a pair of opposing sidewalls cooperating to partially define said tibial prosthesis recess, wherein said lock body is sized to extending substantially entirely between said opposing sidewalls of said articulating component.

13. The tibial prosthesis of claim 9, further comprising a fastener, wherein said locking means comprises a lock body having at least one bore extending therethrough and said tray component includes a tray bore, said fastener extending at least partially through said at least one bore in said lock body and being received in said tray bore to secure said lock body to said tray component and to lock the rotational and translational position of said articulating component relative to said tray component.

14. The tibial prosthesis of claim 9, wherein said articulating component is captured on said superior surface of said tray component and said articulating component is prevented from translating along said superior surface into a position in which said articulating component is not entirely supported by said superior surface of said tray component.

* * * * *